United States Patent
Alexander et al.

(10) Patent No.: US 9,597,062 B2
(45) Date of Patent: Mar. 21, 2017

(54) MEDICAL DEVICES FOR DELIVERING FLUIDS DURING SURGERY AND METHODS FOR THEIR USE

(75) Inventors: William Allan Alexander, Mercer Island, WA (US); Paul D. Bishop, Fall City, WA (US); Steve R. Carter, Edmonds, WA (US); Alisa M. Littau, Woodinville, WA (US)

(73) Assignee: Mallinckrodt Pharma IP Trading D.A.C. (IE)

( * ) Notice: Subject to any disclaimer, the term of this patent is extended or adjusted under 35 U.S.C. 154(b) by 104 days.

(21) Appl. No.: 12/988,353

(22) PCT Filed: Apr. 27, 2009

(86) PCT No.: PCT/US2009/041772
§ 371 (c)(1),
(2), (4) Date: Dec. 30, 2010

(87) PCT Pub. No.: WO2009/132331
PCT Pub. Date: Oct. 29, 2009

(65) Prior Publication Data
US 2011/0166550 A1 Jul. 7, 2011

Related U.S. Application Data

(60) Provisional application No. 61/125,504, filed on Apr. 25, 2008.

(51) Int. Cl.
*A61B 17/00* (2006.01)
*A61B 17/32* (2006.01)

(52) U.S. Cl.
CPC ...... *A61B 17/00491* (2013.01); *A61B 2017/0065* (2013.01); *A61B 2017/00473* (2013.01);
(Continued)

(58) Field of Classification Search
CPC .......... A61B 17/00491; A61B 17/0057; A61B 2017/00637; A61B 2017/00004;
(Continued)

(56) References Cited

U.S. PATENT DOCUMENTS

| 1,256,831 | A | * | 2/1918 | Rogers | ............. A61B 17/00234 604/1 |
| 1,523,943 | A | * | 1/1925 | Fowle | ................. A61M 3/0279 604/1 |

(Continued)

FOREIGN PATENT DOCUMENTS

| WO | 0139669 A1 | 6/2001 |
| WO | 02064192 A1 | 8/2002 |

(Continued)

*Primary Examiner* — Kevin C Sirmons
*Assistant Examiner* — William Carpenter

(57) ABSTRACT

Provided is a surgical applicator and applicator tip configured to attach in fluid communication, for the delivery of beneficial fluids. The applicator tip may also be configured to reversibly attach, in fluid communication, with a pledget. For example, the applicator tip may include male or female threads, and the pledget has threads that are complementary to the thread configuration of the tip. The applicator tip may further comprise at least one fluid transfer lumen for transfer of a fluid from the tip to the pledget. In one embodiment of the invention, the tip includes male threads and the pledget includes a pledget attachment portion. There are also provided methods for connecting the tip to the pledget. In one embodiment, a tip comprising male threads is attached to the pledget, comprising a pledget attachment portion, by tapping or pressing the tip into the pledget attachment portion. There are also provided methods of use for the attached tip and pledget, including debridement, tissue translocation, delivery of fluid substances, absorption of fluid substances and combinations thereof. In a particular embodiment, the appli- (Continued)

cator places a thrombin solution into the attached pledget for delivery of an active hemostatic agent to a tissue site.

38 Claims, 12 Drawing Sheets

(52) U.S. Cl.
CPC ............... *A61B 2017/00495* (2013.01); *A61B 2017/00654* (2013.01); *A61B 2017/320044* (2013.01)

(58) Field of Classification Search
CPC ... A61B 2017/0065; A61B 2017/0406; A61M 35/006; A61M 35/003; A61M 35/00
USPC ..... 604/82, 83, 187, 191; 1/82, 83, 187, 191
See application file for complete search history.

(56) References Cited

U.S. PATENT DOCUMENTS

| | | | |
|---|---|---|---|
| 1,711,352 A * | 4/1929 | Jeffreys | A61B 10/04 604/1 |
| 3,324,855 A * | 6/1967 | Heimlich | 604/3 |
| 3,481,676 A * | 12/1969 | Schwartzman | 401/134 |
| 3,758,950 A * | 9/1973 | Krouzian | 433/91 |
| 3,935,863 A * | 2/1976 | Kliger | A61F 13/38 604/267 |
| 3,936,863 A * | 2/1976 | Olmstead | 257/539 |
| 4,040,420 A | 8/1977 | Speer | |
| 4,158,916 A * | 6/1979 | Adler | 433/91 |
| 4,329,990 A * | 5/1982 | Sneider | 604/2 |
| 4,332,250 A * | 6/1982 | Behney | 604/517 |
| 4,359,049 A | 11/1982 | Redl et al. | |
| 4,415,288 A * | 11/1983 | Gordon et al. | 401/132 |
| 4,498,796 A * | 2/1985 | Gordon et al. | 401/132 |
| 4,874,368 A | 10/1989 | Miller et al. | |
| 4,900,303 A * | 2/1990 | Lemelson | 604/514 |
| 4,902,281 A | 2/1990 | Avoy | |
| 4,978,336 A * | 12/1990 | Capozzi | A61B 17/00491 222/137 |
| 5,116,315 A | 5/1992 | Capozzi et al. | |
| 5,203,767 A * | 4/1993 | Cloyd | A61F 13/36 604/11 |
| 5,368,563 A | 11/1994 | Lonneman et al. | |
| 5,372,585 A * | 12/1994 | Tiefenbrun | A61M 31/00 604/57 |
| 5,474,540 A | 12/1995 | Miller et al. | |
| 5,476,777 A * | 12/1995 | Holly et al. | 435/214 |
| 5,843,017 A | 12/1998 | Yoon | |
| 5,928,611 A * | 7/1999 | Leung | A61B 17/00491 422/131 |
| 6,183,497 B1 * | 2/2001 | Sing et al. | 606/213 |
| 6,228,051 B1 | 5/2001 | Trumbull | |
| 6,309,375 B1 | 10/2001 | Glines et al. | |
| 6,315,753 B1 * | 11/2001 | Cragg et al. | 604/15 |
| 6,428,234 B1 | 8/2002 | Bobo et al. | |
| 6,439,789 B1 | 8/2002 | Ballance et al. | |
| 6,884,232 B1 * | 4/2005 | Hagmann | A61B 17/00491 604/191 |
| 6,921,381 B2 | 7/2005 | Spero et al. | |
| 8,083,425 B2 * | 12/2011 | Kaufman et al. | 401/133 |
| 2002/0072767 A1 * | 6/2002 | Zhu | 606/213 |
| 2002/0165483 A1 | 11/2002 | Miller et al. | |
| 2003/0069537 A1 | 4/2003 | Spero et al. | |
| 2004/0102730 A1 | 5/2004 | Davis et al. | |
| 2004/0265040 A1 * | 12/2004 | Rosenberg | 401/203 |
| 2004/0267180 A1 * | 12/2004 | Beaudry | 604/1 |
| 2005/0085796 A1 * | 4/2005 | Wells | 604/890.1 |
| 2005/0096588 A1 * | 5/2005 | Hagmann et al. | 604/82 |
| 2005/0148963 A1 * | 7/2005 | Brennan | 604/364 |
| 2007/0005007 A1 | 1/2007 | Hoogenakker et al. | |
| 2007/0049860 A1 | 3/2007 | Seminara | |
| 2007/0219497 A1 * | 9/2007 | Johnson | A61M 1/0092 604/131 |
| 2009/0306776 A1 * | 12/2009 | Murray | 623/13.12 |
| 2010/0280312 A1 * | 11/2010 | D'Alessio | A61B 17/00491 600/104 |

FOREIGN PATENT DOCUMENTS

| | | |
|---|---|---|
| WO | 2006/064285 A1 | 6/2006 |
| WO | WO2007064906 A2 | 6/2007 |

* cited by examiner

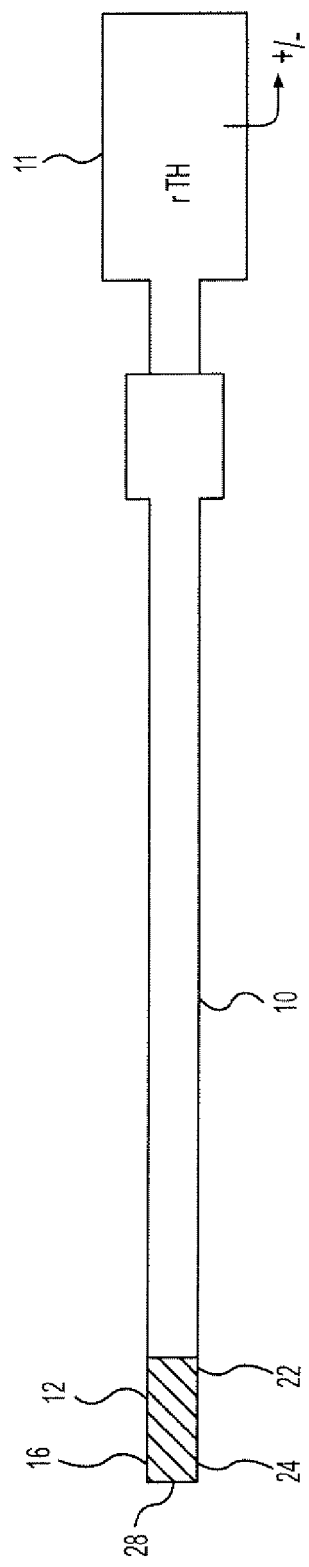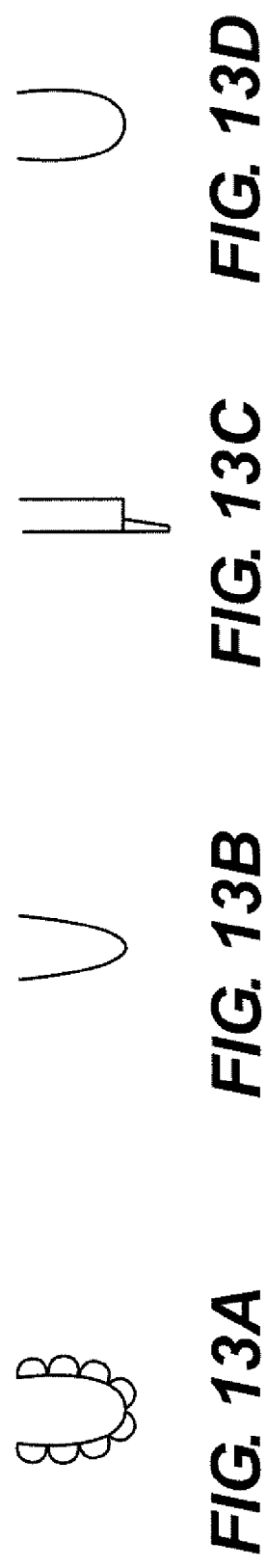
FIG. 13
FIG. 13A  FIG. 13B  FIG. 13C  FIG. 13D

MEDICAL DEVICES FOR DELIVERING FLUIDS DURING SURGERY AND METHODS FOR THEIR USE

RELATED APPLICATIONS

This application claims the benefit of U.S. Patent Application Ser. No. 61/125,504, filed Apr. 25, 2008, which is incorporated herein by reference.

FIELD OF THE INVENTION

This invention relates generally to devices and methods for focused delivery of fluids, such as hemostatic agents, during surgery. More particularly, this invention provides for applicator tips configured to attach to an applicator and, optionally, a pledget or other porous matrix, and configured to deliver a fluid to a desired site during surgery. Various aspects address continual diffusion of fluid thru the tip or tip/pledget during surgery, allowing for precise application to a tissue with or without concurrent pressure application.

BACKGROUND

A particular challenge presented in surgical instrumentation relates to the delivery of non-viscous or viscous solutions such as pharmaceutical agents, hemostatic solutions, anti-adhesives, wound-healing agents, analgesics, and the like. Non-viscous solutions can be sprayed into a surgery site using various instruments, but the solutions often drip off desired target site and pool in the body cavity before the active component can provide its intended benefit. For example, when bleeding occurs during surgery, it may obstruct the surgeon's vision, and increase patient risks from loss of blood. Thus, the surgeon may deliver an active hemostat component, such as thrombin compositions reconstituted in saline, or other tissue sealant to a bleeding target site. For example, a thrombin solution can be sprayed into an insufflated lumen using a laparoscopic tool, but the solution typically does not adhere to the bleeding target site and instead pools to the floor of the cavity. In contrast, a more viscous, tacky thrombin solution may adhere better to a bleeding target site, but such viscous solutions are often opaque and obstruct the surgeon's view. Hence, there remains a need for a fluid-delivery apparatus for use in surgery for administering a continuous infusion of beneficial fluids, such as thrombin solutions, optionally with the application of pressure, at the site in need.

Tissue sealants (or tissue adhesives) are used for providing hemostasis and closing incisions during many surgical procedures. Tissue sealants may include fibrin, comprised of thrombin and a fibrinogen material, although other multiple component materials are available. Tissue adhesives for making fibrin clots use different concentrations of fibrinogen solution in conjunction with a thrombin solution. Depending upon the percentages of fibrin and thrombin in each respective tissue adhesive solution, as well as the other components found in each solution, various factors impact the mixing and application of the components. These factors include viscosity of the initial fibrinogen and thrombin solutions and of the final mixed solution. When mixed together, thrombin and fibrinogen components usually coagulate very quickly, often yielding an adhesive gel within 10 or 20 seconds. When applied to a body's exterior, or when considerable access to the application site is possible, the tissue sealant's rapid coagulative properties are welcomed. Conversely, when a fibrin sealant is used during internal surgical procedures, such fast-acting properties may cause problems such as fouling or clogging of the applicator device during application.

Additionally, other considerations for laparoscopic instrument-based delivery of fibrin sealants include diameters or sizes of the fluid passages and the mixing compartment of the laparoscopic instrument, and mixing rate of the fibrinogen and thrombin solutions particularly in comparison to ejection rate if mixing occurs within the system. Typically, the individual components of the adhesive material are stored in isolated reservoirs.

There remains a need, however, for a fluid applictor system that is useful in surgery for delivering viscous fluids, or fluids that should be well-mixed for maximal activity. There is also a need for an applicator tip useful for both applying the fluid and holding it against the target site with a desired amount of pressure. Additionally, in particular cases, it may be beneficial to leave a biodegradable, bioadsorbable, fluid-laden applicator tip or pledget at a desired surgical site as a sustained release implant.

SUMMARY OF THE INVENTION

It is desirable to develop devices and methods for delivering fluids of any viscosity during general surgeries and minimally invasive procedures. Such devices may use standard available instruments for their preparation and application; produce an improved output for delivery of a fluid; and, when necessary, provide for fluid or agent mixing. Such a system has a wide variety of uses in the medical field. Thus, for example, there is a need for a device capable of effectively delivering a multi-component tissue sealant to a location in vivo from a remote location, with optional concurrent pressure application.

An aspect of the present invention provides for applicators, useful during surgeries, for delivering to a target site one or more fluids at a range of viscosities. The distal end of the applicators can be connected to an applicator tip and/or a pledget or other porous matrix material, or, optionally, the distal end of the applicator can be constructed similarly to a desired pledget. A variety of porous pledgets (both bioabsorbable and non-absorbable) and construction thereof are incorporated by this disclosure. Thus, the distal end of the applicator can be connected to, or, optionally, constructed similarly to such dissector sponges.

These applicators allow for the delivery of low viscosity fluids to a target site by holding the fluid at the distal end of the applicator. For example, a thrombin composition reconstituted in saline is often a low viscosity solution. In one embodiment, the low viscosity fluid is maintained within the porous matrix the pledget or distal end of the applicator tip when constructed of a porous matrix similar to a pledget. The pledget or applicator tip may then be pressed to the target site and the low viscosity solution is brought in contact with the target site where its active components can operate. Thus, the low viscosity fluid is delivered to the intended site, avoiding the problem of fluid draining away from the site before activity takes place and providing a means to apply concurrent pressure. In addition, the fluid-laden pledget can be used to deliver the solution into sites that are difficult to access.

Similarly, the applicators encompassed herein allow for the delivery of multiple fluids to a target site. Different fluids can have different viscosities and/or can be rapidly reactive. For example, pharmaceutical agents (e.g., fibrinogen solution and thrombin solutions) may have different viscosities, thus preventing ease of mixing in a external sprayed stream.

Moreover, some reactive pharmceuticals (e.g., thrombin and fibrinogen) will rapidly react (e.g., form fibrin clots) when admixed, thus stymieing internal mixing. In certain embodiments of the instant invention, the two pharmaceutical agents remain separated until the two solutions enter the pledget (or distal end of the applicator tip if tip is constructed similarly to a pledget). At this point, the two solutions can properly mix outside the applicator without clogging the applicator. The pledget or tip is then pressed to the target site and the pharmaceutical agents are brought in contact with the target site, where they can provide benefit.

According to these and other aspects of the present invention there is provided a device for delivery of a fluid including an applicator having at least one lumen housed within the applicator, the applicator having a proximal end and a distal end, and an applicator tip having a proximal end and a distal end. The applicator tip proximal end includes at least one fluid delivery channel or semi-permeable material capable of fluidly connecting to the at least one lumen or fluid delivery tube in the applicator. The applicator tip distal end includes the at least one fluid-permeable material or an opening. The applicator distal end and the applicator tip proximal end are configured to detachably coupled to each other.

According to these and other aspects of the present invention there is also provided a method of delivering a fluid to a target site within a body cavity comprising coupling an applicator tip proximal end to an applicator distal end, wherein the applicator and applicator tip are in fluid communication. The applicator tip is contacted to a target site and at least one fluid from at least one source is delivered through the applicator to the applicator tip to the target site.

These and other features, aspects, and advantages of the present invention will become more apparent from the following detailed description.

BRIEF DESCRIPTION OF THE DRAWINGS

FIG. 13 is a perspective view a manual or automated liquid applicator and tip configuration.

FIGS. 13A-13D are alternative tip configurations for the applicator of FIG. 13.

DETAILED DESCRIPTION

Figure 1:
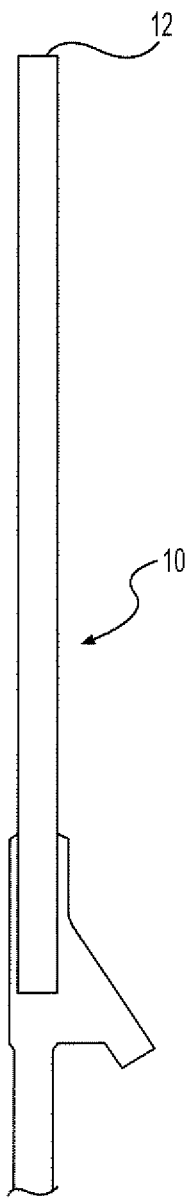
FIG. 1 is a cross-sectional view of an example applicator.

It should be understood that this invention is not limited to the particular methodology, protocols, and reagents, etc., described herein and as such may vary. The terminology used herein is for the purpose of describing particular embodiments only, and is not intended to limit the scope of the present invention.

As used herein and in the claims, the singular forms "a," "an," and "the" include the plural reference unless the context clearly indicates otherwise. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

To address the problems for delivering various fluids, such as fibrin sealants, during surgery, numerous tissue adhesive applicators have been developed, such as those referred to in U.S. Pat. No. 4,040,420; U.S. Pat. No. 4,359,049; U.S. Pat. No. 4,874,368; U.S. Pat. No. 4,902,281; U.S. Pat. No. 4,978,336; U.S. Pat. No. 5,368,563; and U.S. Pat. No. 5,474,540. A variety of types of these applicators exist including internal swirl or mixing chamber applicators, and external combining applicators such as external swirl applicators and external spray or stream overlapping applicators. U.S. Pat. No. 5,116,315 and U.S. Pat. No. 6,921,381, herein incorporated by reference, describe swirl or other pre-ejection mixing applicators where mixing is performed by squirting or otherwise forcing both fluids into a chamber where the fluids mix, to some degree, based on turbulence in the chamber and the material properties, and are thereafter ejected from the applicator. In short, the mixing occurs inside the applicator and thus time is critical the contents must be ejected prior to coagulation. In some applications such as where one or more of the solutions or fluids is thick or highly viscous, internal swirling results in only marginal or partial mixing; although in other applications such as where all of the solutions or fluids are thin or not-highly viscous, substantial and effective mixing occurs.

In contrast, the applicators in U.S. Pat. No. 4,040,420; U.S. Pat. No. 4,874,368; U.S. Pat. No. 4,902,281; U.S. Pat. No. 5,368,563; and U.S. Pat. No. 5,474,540 and U.S. Published Patent Application No. 2002/0165483 and No. 2007/0005007, are external combining applicators. The '563 patent relates to an external mixing device where each fluid is sprayed in a swirl pattern that overlaps the other fluid's swirl pattern resulting in fluid mixing. In contrast, the '368 and '540 applicators eject streams that intersect, whereby the fluids combine. External combining is the process of bringing the two solutions into contact with one another at the point of use for functional tissue adhesive creation. External combining eliminates premature mixing problems. With many external combining applicators, thorough mixing of the solutions does not occur, however, and instead only adjacent portions of the solutions mix while large percentages remain unmixed. This results in inefficient and somewhat uncontrolled coagulation. Moreover, many fibrin glue solutions contain at least one highly viscous component and are thus not readily nor effectively combined in an external manner, as the viscous solution does not combine or mix with the other solution whether it be thin (non-viscous), thick, or highly-viscous. In addition, highly viscous fluids often are difficult to expel or otherwise push out of a syringe or other storage chamber used in surgeries. This is particularly true when the syringes are actuated manually, and in designs with small diameter passages or channels which are typical in surgery, especially minimally invasive (e.g., laparoscopic) surgery. Moreover, the problem of adequate external mixing is applicable whether actuation is manual or via pressure from a compressed gas.

Provided herein are applicators useful during both general and minimally invasive (e.g., laparoscopic) surgeries for delivering to a target site one or more fluids at a range of viscosities. The distal end of the applicator can be connected to a pledget, or, optionally, the distal end of the applicator can be constructed to include a desired pledget. A variety of pledgets and the construction thereof are incorporated by this disclosure. For example, such pledgets include cotton and gauze, sponge, fused gelatin beads, gauze, plastic or any suitable porous material, either bioadsorbable or non-bioadsorbable, or a combination thereof. One commercial pledget is the AUTO-COUNT® Dissector Sponge (Fabco, New London, Conn.). Thus, the distal end of the applicator tip can be connected to, or, optionally, constructed similarly to such dissector sponges. The applicators, therefore, allow for the delivery of low viscosity fluids to a target site by holding the fluid at the distal end of the applicator tip. For example, a thrombin composition reconstituted in saline is often a low viscosity solution. In the instant invention, the low viscosity fluid is maintained within the pores of the pledget, or distal end of the applicator when the tip is constructed of a material similar to a pledget. In use, the pledget or applicator tip is pressed to the target site and the low viscosity solution brought in direct contact with the site, wherein its active components can operate. Thus, the low viscosity fluid is delivered to, and maintained at, the intended site, avoiding the problem of draining away before beneficial activity occurs.

Similarly, the applicators of the present invention allow for the delivery of multiple fluids to a target site. Different fluids can be of varying viscosities and/or can be rapidly reactive. For example, fibrinogen solution and thrombin solution are typically two solutions with differing viscosities that are not mixed easily in an external sprayed stream, and that rapidly form fibrin clots when admixed, which makes internal mixing problematic. In certain embodiments of the instant invention, the thrombin solution and the fibrinogen solution remain separated until the two solutions enter the pledget (or distal end of the tip if the distal end of applicator tip is constructed similarly to a pledget). At this point, the two solutions can mix properly, externally to the applicator (such as a laparoscopic applicator device), without clogging the device. The pledget or tip is then pressed to the target site, deliverying the fibrinogen/thrombin solution to the target site wherein it can operate.

Figure 2:
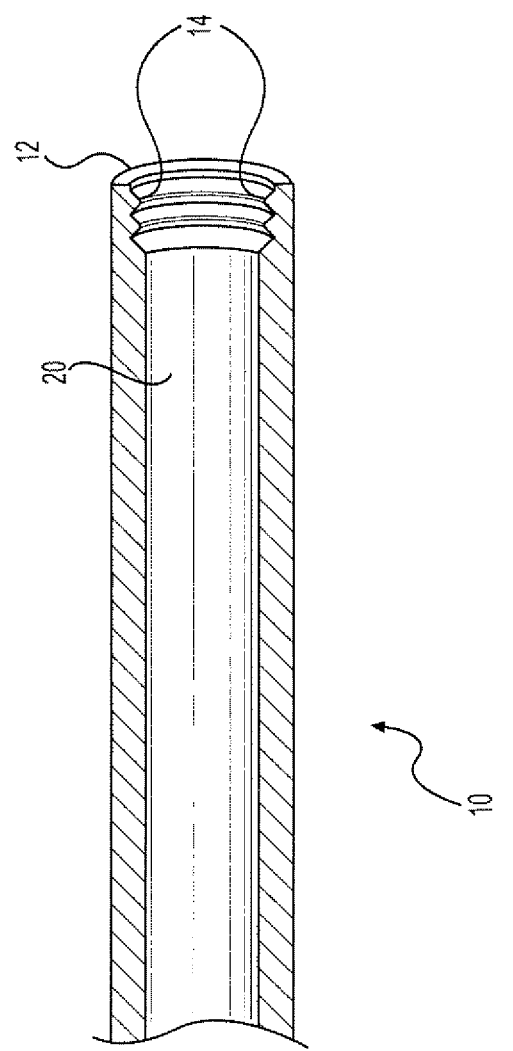
FIG. 2 is an enlarged cross-sectional view of a distal end of an applicator according to the present invention.

Referring to FIG. 1, an applicator 10 has a distal end 12. FIG. 2 shows an exploded view of the distal end 12 of applicator 10. The applicator 10 may be made of plastic or metal or any suitable material that can be sterilized for use in surgery and constructed by typical known approaches. It may be re-usable or disposable. In the embodiment of FIG. 2, the distal end 12 includes female threads 14 for attachment to a complementary pledget or applicator tip. The applicator 10 also defines a fluid delivery lumen 20. Alternatively, the interior of the applicator may define two or more lumen, or house at least one fluid delivery tube within the lumen.

Applicator 10 may have a diameter of and about 5-15 mm, about 10-20 mm or about 5-2 mm. The applicator may have a length of and about 30-50 cm or about 20-40 cm. For example, in specific variations, the length is about 30 cm, about 40 cm, or about 45 cm.

Figure 3:
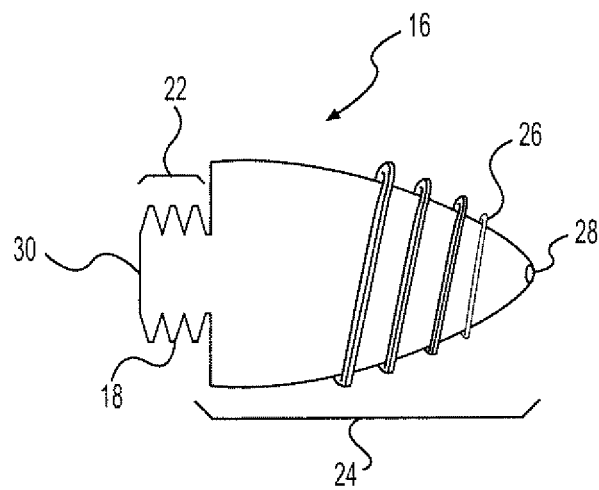
FIG. 3 is a perspective view of one embodiment of an applicator tip according to the present invention.
Figure 4:
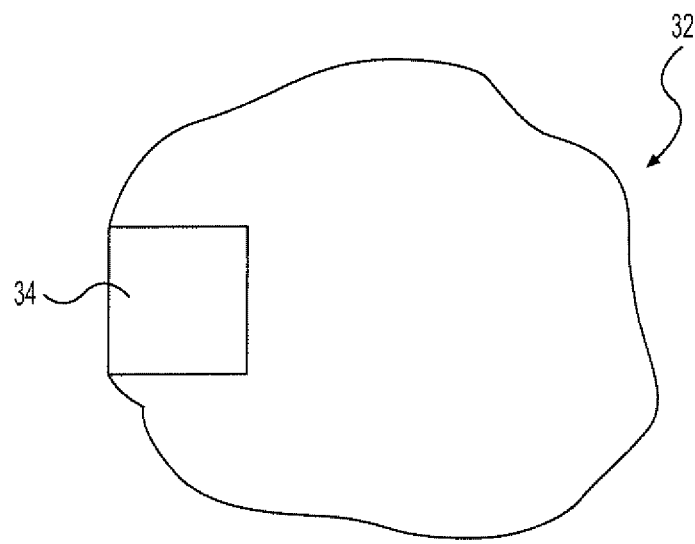
FIG. 4 is a perspective view of a pledget.

FIG. 3 shows an example of an applicator tip 16 that has male threads 18 at its proximal end 22. Thus, for example, the proximal end 22 male threads 18 complement the female threads 14 of the distal end 12 of applicator 10. The tip 16 also includes a fluid delivery lumen 30, running from the proximal end 22 to the distal end 24 of the tip 16 to the delivery port 28. Thus, applicator tip 16 includes a fluid delivery port 28, in communication with the fluid delivery lumen 30. Additionally, applicator tip 16 includes male threads 26 on the distal end 24 for optional attachment to a pledget. For example, the pledget 32 in FIG. 4 includes an attachment portion 34, into which the teeth of the male threads 26 of tip 16 may 'bite' to secure the pledget onto the applicator 10 distal end 12. The pledget 32 is made of any suitable porous material through which fluid will pass from fluid delivery port 28, as described herein.

Tip 16 may have a diameter of about 5-15 mm or about 5-12 mm and a length of about 5-15 mm, about 10-20 mm or about 15-25 mm.

Figure 5A:
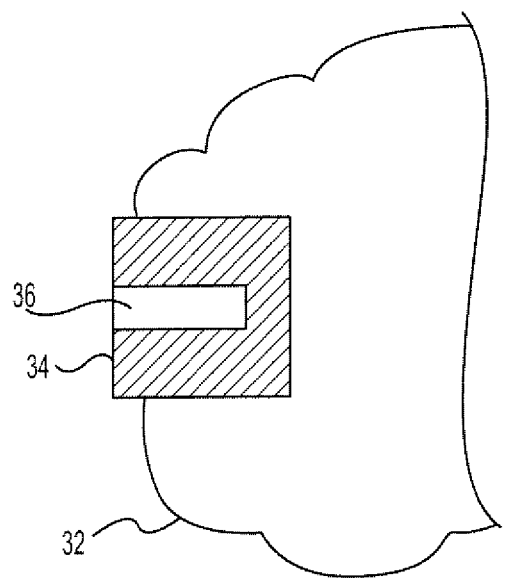
FIG. 5*a* is a perspective view of another embodiment of a pledget.
Figure 5B:
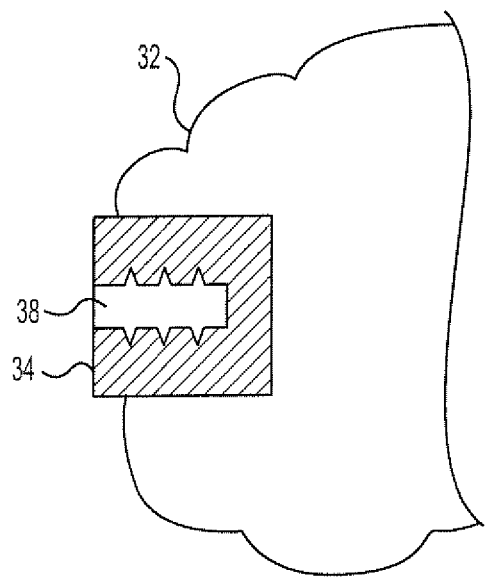
FIG. 5*b* is a perspective view of ayet nother embodiment of a pledget.

Additionally, attachment portion 34 may attach to a variety of applicators or applicator tips, not necessarily requiring male threads. Thus, for example, as shown in FIG. 5a, the pledget 32 may include attachment portion 34 having a non-threaded shaft 36, or a threaded shaft 38 as shown in FIG. 5b.

Figure 6:
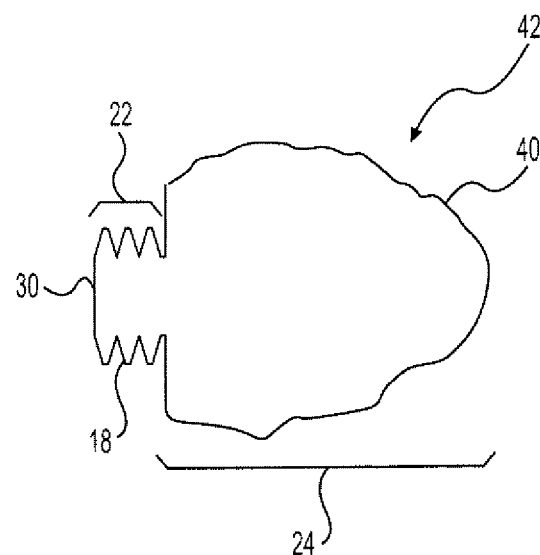
FIG. 6 is a cross-sectional view of an applicator according to the present invention.

FIG. 6 illustrates a single applicator tip 42 of the current invention, having a proximal end 22 and a distal end 24. The proximal end of the tip 22 includes male threads 18 and at least one fluid delivery lumen or channel 30. The distal end of the applicator tip 24 and 40 is configured to take the place of the pledget described in other embodiments. Thus, in this particular aspect, the material comprising 40 is a pledget-like material. This example tip 42 could be attached to applicator 10 by the complementary female threads 14 housed within the applicator distal end 12, which example structures are shown in FIGS. 1 and 2.

The above embodiment(s) provides for a device for delivery of a fluid, comprising: (a) an applicator tip proximal end capable of detachably coupling to an applicator, such as a laparoscopic applicator; (b) an applicator tip distal end capable of coupling to a pledget attachment portion; (c) at least one fluid delivery lumen or channel at the tip proximal end capable of fluidly connecting to at least one lumen or fluid delivery lumen or tube within the applicator; and (d) at least one fluid delivery opening at the applicator tip distal end capable of fluidly connecting to a pledget. For example, the tip proximal end is configured to detachably couple to the applicator device by a threaded or a pressure coupling.

In one aspect of this embodiment, the applicator tip's delivery lumena are configured to fluidly couple to a applicator's lumen or fluid delivery tube. In this aspect, in which the applicator has one lumen, a tip can have one fluid delivery lumen for fluid connection. Alternatively, an applicator may have one fluid delivery lumen or tube, and a tip may have at least two fluid delivery lumena, both of which fluidly connect with the applicator lumen or fluid delivery tube. Further, an applicator may have one fluid delivery lumen or tube and a tip one fluid delivery lumen in fluid contact. Or, an applicator may have two fluid delivery lumena or tubes, and a tip has two fluid delivery lumena, each fluidly connected applicator-to-tip. The fluid delivery lumen of the tip can be branched or single channel. Thus, the applicator tips may be configured to bring at least one fluid delivery lumen of the tip into fluid contact with at least one fluid delivery lumen of the applicator.

When the applicator of the current invention is configured to bring a fluid delivery lumen of the tip and a fluid delivery lumen of the applicator into fluid contact, the tip may be configured to properly align each channel to its respective position. Such alignment is useful to prevent premature mixing of solutions. For example, this can be a problem when two solutions are intended to be separated and those two solutions are fibrinogen solution and a thrombin solution: premature mixing may cause clotting of the device. Thus, one embodiment provides for an indicator mark on the tip that is configured to align with an indicator mark on an applicator. The indicator mark can be used to indicate, for example, that a first fluid delivery lumen of the tip is aligned with a first fluid delivery lumen of the applicator and a second fluid delivery lumen in the tip is aligned with a second fluid delivery lumen in the applicator.

Alternatively, the tip can be configured with a position locking member complementary to a position locking member on the applicator, wherein the position locking member is configured, when locked, to place the first fluid delivery lumen in the tip in alignment with a first fluid delivery lumen in the applicator, and a second fluid delivery lumen in the tip in alignment with a second fluid delivery lumen in the applicator. In this embodiment, the applicator tip may be configured to attach to a pledget. The attachment may not be releasable in instances where it is not desirable to leave material within a surgery site. There are instances, however, where the pledget can be releasably attached to the applicator tip. Hence, the pledget may be made of a biodegradable, biocompatible, and/or porous material. In certain embodiments, the pledget may further contain a radio-opaque material, which can facilitate, e.g., locating the pledget during and/or post-surgery.

FIG. 6 illustrates a single applicator tip 42 of the current invention, having a proximal end 22 and a distal end 24. The proximal end of the tip 22 comprises male threads 18 and at least one fluid delivery channel 30. The distal end of the applicator tip 24 and 40 is configured to take the place of the pledget described in other embodiments. Thus, this particular aspect, the material comprising 40 is a pledget-like material. This example tip 42 could be attached to applicator 10 by the complementary female threads 14 housed within the applicator distal end 12, which example structures are shown in FIGS. 1 and 2.

As described above, the applicator tip distal end can include male threads. In this aspect, the pledget can comprise complementary female threads at the pledget attachment portion. Alternatively, the pledget can comprise a non-threaded cavity at the pledget attachment portion, useful for attachment by tapping the tip into the pledget attachment portion, as shown in FIG. 5A. Principles of tap and die are known in the art. A similar configuration employs a click-on/pop-off mechanism in which the pledget comprises a flange for securing it inside the distal end of an applicator having multiple spring arms with teeth that retain the pledget flange. The applicator can include a release mechanism, such as a bulb, that when advanced retracts the spring arms and pushes the pledget forward, releasing the pledget. Alternatively, the pledget attachment portion can have the male threads and the tip configured with female threads or a non-threaded cavity. Other mechanical attachments useful with the current invention are well known in the art.

Figure 7:
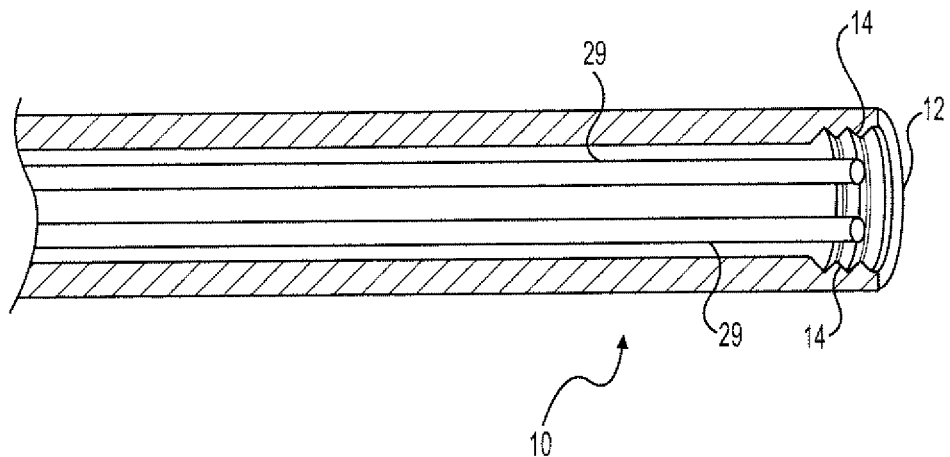
FIG. 7 is a cross-sectional view of a distal end of another applicator according to the present invention.

In another embodiment, FIG. 7 illustrates a cross-sectional view of a distal end 12 of applicator 10 further illustrating female threads 14, which can be used for detachably coupling the applicator to an applicator tip of the invention. In this embodiment, the applicator 10 houses a pair of fluid delivery lumena, in this embodiment tubes 29. Thus, in attachment with tip 42 via female threads 14 and male threads 18, fluid delivery tubes 29 achieve fluid communication with fluid delivery lumen 30. When fluid delivery tubes 29 each contain a different agent, these agents are mixed within the delivery lumen 30 and the pledget material 40.

Alternatively, two fluid delivery lumena may be housed in the applicator tip, and in such case the applicator 10 and applicator tip 16 may bear complementary marks used to indicate when the applicator fluid delivery tubes are aligned with the fluid delivery lumen(a), such that the tubes and channels are in fluid communication. In this embodiment, the two fluids are mixed within the pledget or when otherwise expelled from the applicator tip.

Figure 8:
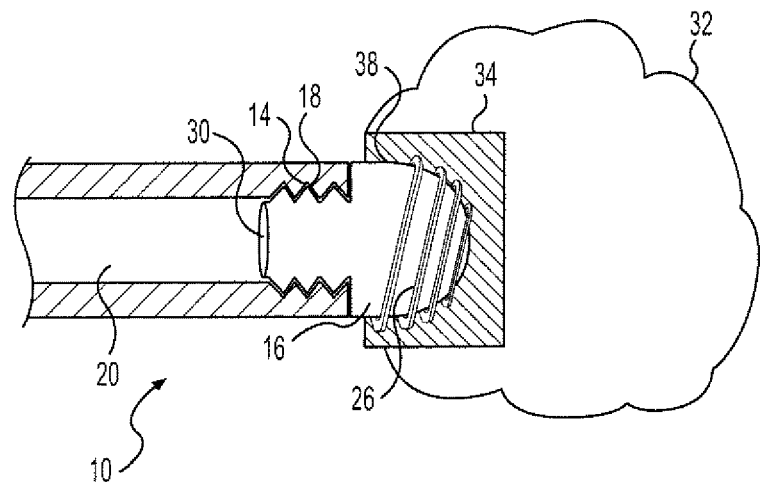
FIG. 8 is a cross-sectional view of another distal end of an applicator detachably coupled to a tip, which is in turn couples to a pledget according to the present invention.

An example of an application 10 attached to a tip 16, and a pledget 32 is shown in FIG. 8. Also shown in FIG. 8 is the fluid delivery tube 20 and female threads 14 of the applicator 10, which in this figure are mated with the male threads 18 of tip 16, as the male threads 26 of tip 16 are embedded in the pledget attachment portion 34 of pledget 32. In this fashion, fluid lumen 20 is in fluid communication with the lumen 30 of the tip 16, which is in fluid communication with pledget 32 for delivery of active agent. Note that such configurations function for applicators in which fluid are delivered through the lumen of the applicator.

Figure 9:
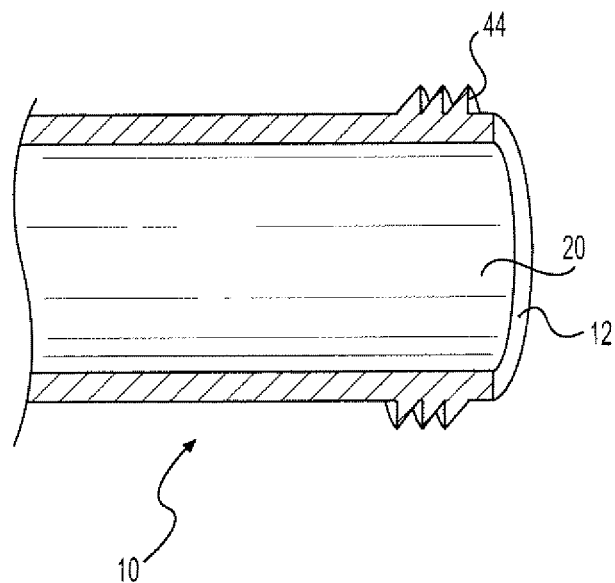
FIG. 9 is a cross-sectional view of another embodiment of attachment of a pledget to an applicator according to the present invention.
Figure 10:
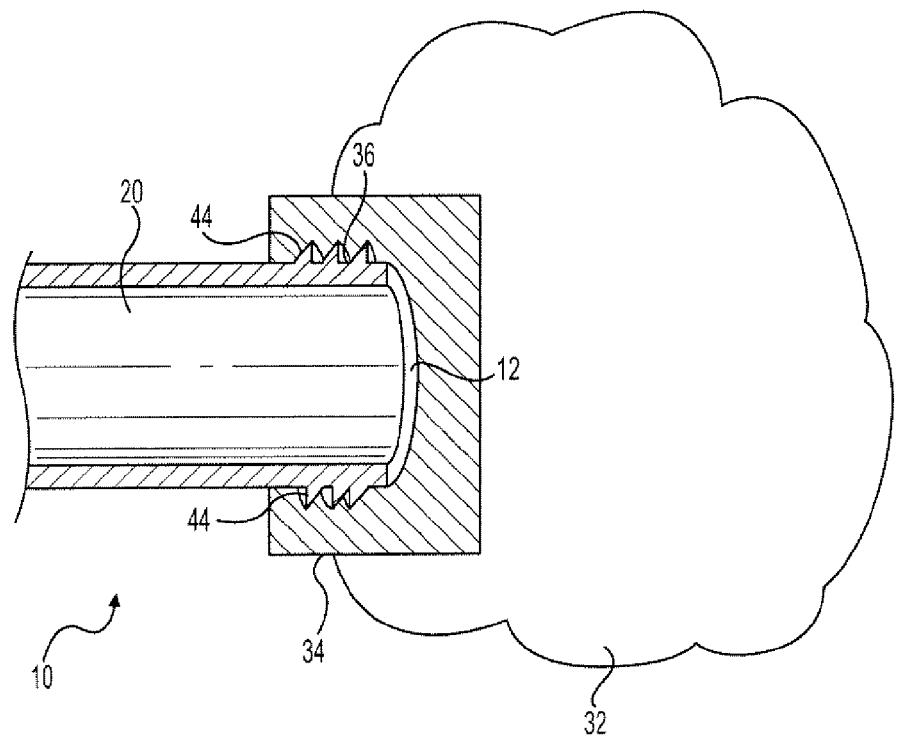
FIG. 10 is a cross-sectional view of another pledget attachment embodiment for an applicator according to the present invention.

FIG. 9 illustrates an alternative embodiment for attaching a pledget attachment portion 34 to an applicator 10, comprising male threads 44 are present in the outer surface of the distal end 12 of the applicator. In this embodiment, the applicator-to-pledget connection is shown in FIG. 10, in which the tip 10 male threads 44 are embedded in the non-threaded shaft 36 of the attachment portion 34 of the pledget 32. In this embodiment, the fluid delivery tube 20 of applicator 10 is in direct fluid communication with the porous material of pledget 32.

Figure 11:
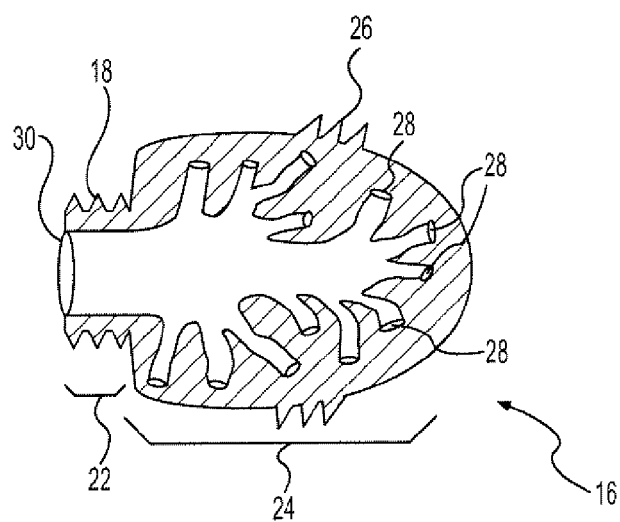
FIG. 11 is a cross-sectional view of another tip or pledget according to the present invention.

Another embodiment of an applicator tip is shown in FIG. 11. The applicator tip 16 includes male threads 18 at the proximal end 22, and a single fluid delivery channel 30 that is branched to provide a plurality of fluid delivery subchannels 28 in the distal end 24 of the tip 16. In this tip embodiment, the fluid delivery openings from subchannels 28 may reach the surface of the tip or they may end internally, depending on the porosity of the material shaping the distal end 24. Additionally, the distal portion 24 of the tip 16 includes male threads 26.

Thus, the applicator tip can include a male threading at its distal end and at least one fluid delivery lumen, each of which form a fluid delivery opening at the tip distal end. Alternatively, the tip may include male threading at its distal end and one fluid delivery lumen, which forms a fluid delivery opening at the tip distal end. These lumena may be branched to distribute a fluid throughout the pledget, or they can be a single lumen to deliver a concentrated fluid bolus. When branched, each of the branched lumena preferably forms a delivery opening at the tip distal end.

In another embodiment, the applicator tip comprises a male threading at its distal end and two fluid delivery lumena, wherein each of the two fluid delivery lumena form a fluid delivery opening at the applicator tip distal end, and wherein at least one of the two fluid delivery lumena is a branched fluid delivery channel and each of the branches forms a delivery opening at the tip distal end. When branched, each of the branches may form a delivery opening at the tip distal end.

Figure 12:
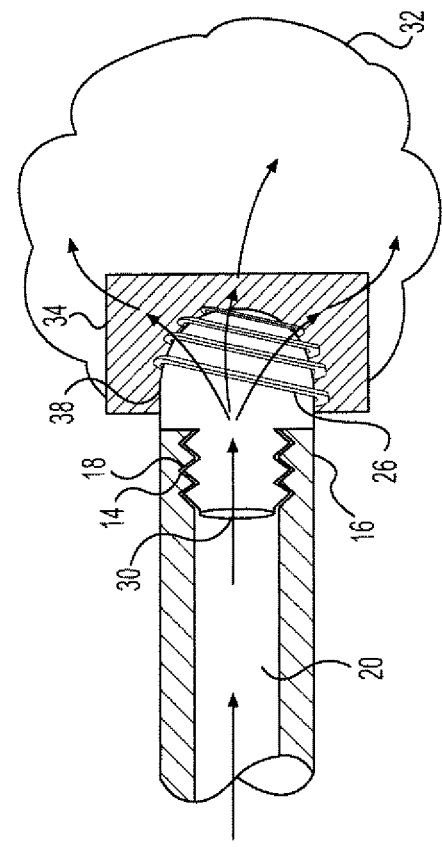
FIG. 12 is a cross-sectional view of an assembly of a fluid source, tip and pledget according to the present invention.
Figure 12:
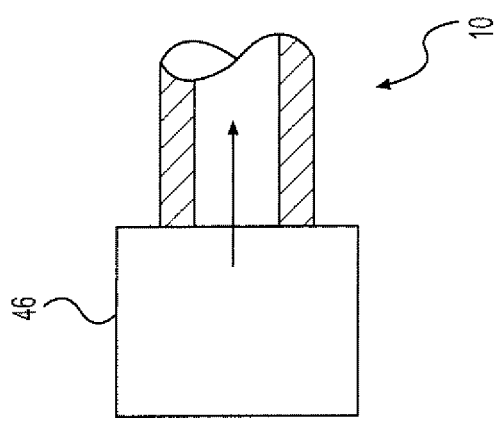

FIG. 12 shows an embodiment in which the applicator 10 includes at least one fluid source 46, a tip 16, and a pledget 32. Black arrows indicate the flow of fluid(s) from a source 46. The fluid is shown dispersing through the applicator fluid lumen 20 to the the tip 16, and through the pledget attachment portion 34. This disbursement can be via multiple and/or branched fluid delivery lumena in the tip and lumena in the pledget attachment portion. Alternatively, the pledget attachment portion can comprise a porous matrix material.

FIG. 13 depicts an embodiment of a manual or automated liquid applicator 10 and several alternative tip configurations. The +/− symbol at the proximal end of the applicator indicates that other pharmaceutical agents may optionally be used in addition or as an alternative to the recombinant human thrombin (rTH) in particular variations of the invention. In this embodiment, the fluids are held in a reservoir 11, that may be attached to applicator 10. The tip 16 is attached to the distal end 12 of the applicator 10 and has a proximal end 22 and a distal end 24, the distal end 24 having an opening or fluid-permeable material 28 for the release of fluid from the tip 16. The proximal end 22 of the applicator tip 16 reversibly attaches to the distal end 22 of the applicator 10 by any number of configurations. The tip 16 may consist of or include fused gelatin beads 13a; sponge 13b; an open tip for flowable pharmaceuticals 13c; cotton 13d, shown in FIGS. 13A-13D, or other suitable materials known in the art. Each of the forgoing may be designed as screw-on tips, for example.

Figure 14A:
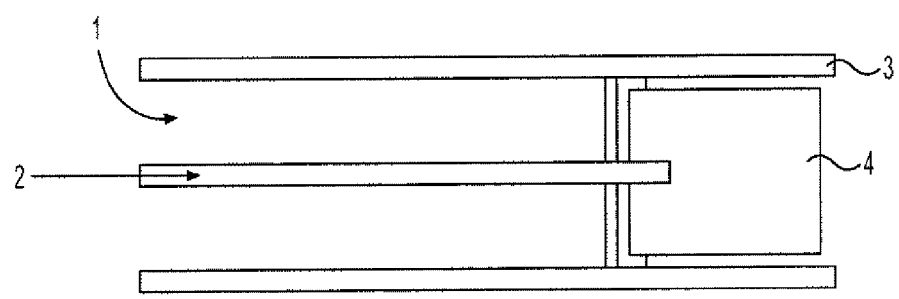
FIGS. 14A and 14B are cut-away views of a distal end of another applicator embodiment.
Figure 14B:
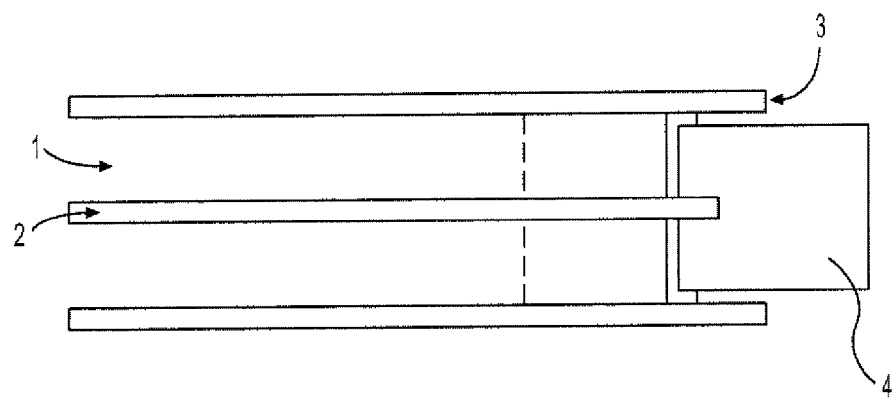

Another embodiment of the applicator is shown in FIGS. 14A and 14B, showing cut-away views of a distal, tip end of an embodiment, wherein the end comprises a piston. The applicator includes a piston chamber 1 and a fluid delivery tube or lumen 2 in the center of the piston chamber. The piston chamber holds a dry pledget 4 (made of, e.g., cellulose, gelatin, fused gelatin microbeads), which may be retracted, or held in the retracted position within the delivery end 3 (see FIG. 14A). When delivery of active agent is desired, pledget 4 is loaded and extended, delivering active solution (e.g., thrombin such as rThrombin) to the site in need of treatment (see FIG. 14B). Although not shown, in some embodiments the distal end of the piston chamber can have a slight inward taper that can help to secure the pledget within the piston chamber 1.

Figure 15A:
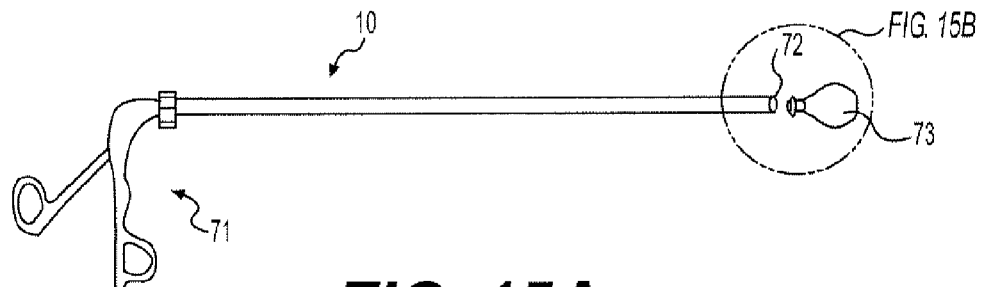
FIGS. 15A-15D show another embodiment of a pledget applicator mount according to the present invention.
Figure 15B:
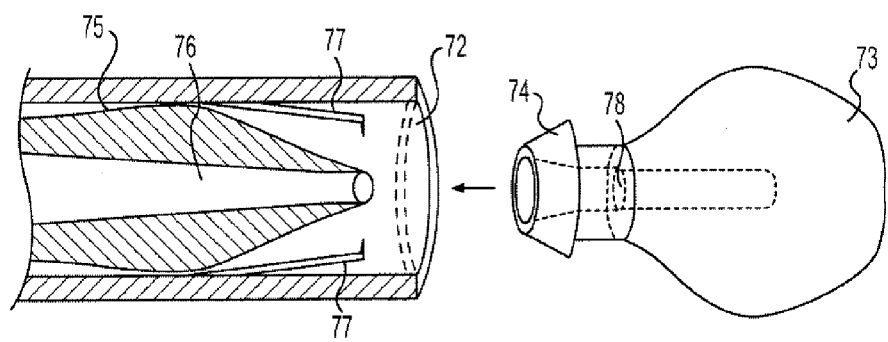
Figure 15C:
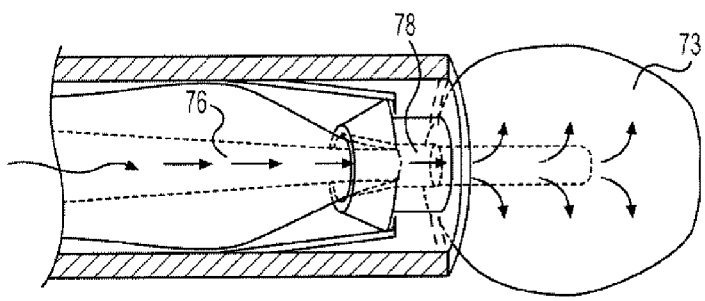
Figure 15D:
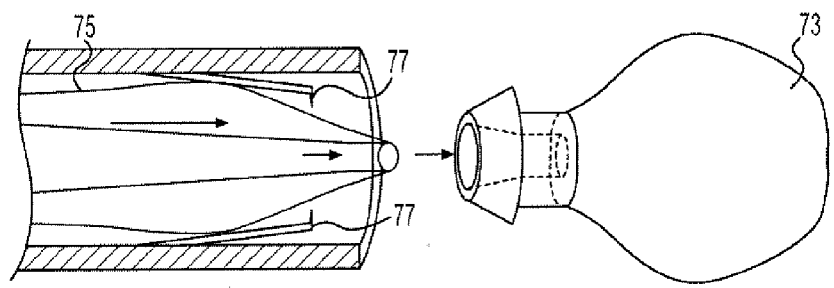

FIGS. 15A-15D show an embodiment in which a pledget 73 with a semi-pliable "flange mount" 74 (made of, e.g., notched cork or plastic) that may be attached to the distal end 72 of the applicator 10 by applying pressure to the proximal end of the flange mount 74 as in FIGS. 15A and 15B. The proximal end of the pledget is then held within the body of the applicator by a spring system that comprises spring arms having retaining teeth 77 that secure the flange, as in FIG. 15C. An interior shaft 75, housed inside the applicator 10, includes a fluid delivery lumen 76 and a tapered tip that fits into the proximal end of the flange mount of the pledget, the flange mount also containing a fluid delivery lumen 78. Liquid is then delivered from the applicator into the pledget. The pledget and mount are removed by advancing the interior shaft 75, which may be "bulb"-actuated, for example be squeezing the handle 71 of the applicator, that serves to retract the spring arms 77 as shaft advances, as shown in FIG. 15D (dashed arrow showing direction of shaft movement). Alternatively, the applicator may have an interior rim at the distal end that will catch and hold the flange mount. The interior shaft, when advanced against the pledget, deforms the flange and allows the shaft to expel the pledget. This mechanism also provides a "click-on/pop-off" method for reloading the applicator with a new pledget.

Figure 16:
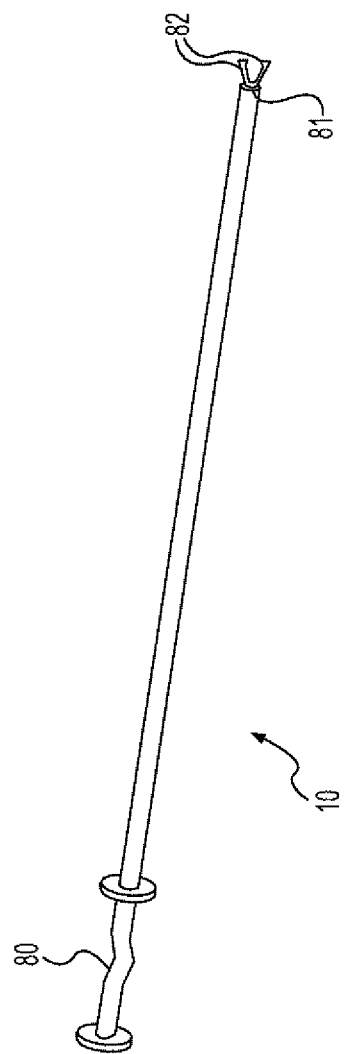
FIG. 16 is a perspective view of another embodiment of an applicator according to the present invention.

A further embodiment is shown in FIG. 16, which depicts an applicator 10 comprising at the distal end 81 at least two prehensile means 82 configured to hold a pledget. The prehensile means 82 are operated by an actuator mechanism 80 at the proximal end of the applicator, which is operably coupled through reciprocating means to the prehensile means 82 at the distal end. The actuator 80 causes the reciprocating means to move between first and second positions, which closes the prehensile means 82 thus providing a means for gripping a pledget. This design holds numerous configurations of pledget. The prehensile means 82 may also comprise small steel balls at the grasping-end, which facilitate releasing cotton pledgets (as opposed to sharper ends that might get stuck in cotton fibers, etc.). The applicator 10 may define an interior lumen or house a fluid delivery tube, to supply solution to the pledget.

As described above, the present invention provides for a pledget that is compatible with the applicator tip of the present invention. Thus, the pledgets include a pledget attachment portion. The pledget attachment portion of the applicator may be a semi-solid material comprising a female threaded shaft, a semi-solid material comprising a non-threaded shaft, a semi-solid material, a gauze-like netting, a cotton fiber, plastic, or combinations thereof. A semi solid material can be a piece of material that is solid except for fluid delivery channels running therethrough. In such an embodiment, the channels, which can be single or branched, are configured for fluid connection to the tip. Alternatively, a semi-solid material can be a matrix material that allows fluids to flow through the matrix as it is extruded towards the remaining pledget material. The pledget attachment portion material may be biodegradable, biocompatible and/or radio opaque. The pledget is a porous, fluid permeable material, such as cotton, gauze, sponge, fused gelatin beads, sponge, or a combination of such materials. Pledget materials are known in the art, and can include, but are not limited to, AUTO-COUNT® Dissector Sponges, gelatin sponges, cellulose sponges, dextran sponges, cotton swabs, gauze wound dressings, fused gelatin spheres, and others, as well as combinations thereof. An example pledget is cotton and gauze and an example pledget attachment portion is a semi-solid material comprising a female-threaded shaft.

An alternative embodiment combines the tip and the pledget into an improved single tip applicator. In this embodiment, the tip is configured to fluidly connect to a surgical (e.g., minimally invasive) device and is further configured to hold a variety of solutions with different viscosities, including low- and high-viscosity solutions, inclusive, and to hold and mix more than one solution wherein the solutions may have different viscosities and/or are rapidly reactive. In this embodiment, there is an applicator for delivery of a fluid includes: (a) an applicator tip proximal end capable of detachably coupling to the distal end of an applicator; (b) at least one fluid delivery lumen at the applicator tip proximal end capable of fluidly connecting to the applicator; (c) an applicator tip distal end further comprising a fluid permeable, porous material. The applicator tip proximal end may be configured to detachably couple to the applicator by a threaded coupling.

In one aspect of this embodiment, the applicator tip's fluid delivery lumena are configured to fluidly couple to an applicator's fluid delivery lumena. In this aspect, wherein a minimally invasive (e.g., laparoscopic) applicator comprises one fluid delivery lumen, the applicator tip may comprise one fluid delivery lumen for fluid connection. Alternatively, an applicator comprises one fluid delivery lumen and a tip comprises at least two fluid delivery lumena, both of which will fluidly connect with the fluid delivery tube. Or, an applicator comprises one fluid delivery lumen and the tip comprises one fluid delivery lumen in fluid contact. Alternatively, an applicator comprises two fluid delivery lumna and its tip comprises two fluid delivery lumena, each fluidly connected. The fluid delivery channels of the tip can be branched or single channel. Thus, the tips of the current invention are configured to bring one or more fluid delivery lumena into fluid contact with one or more fluid delivery lumena of the applicator. Fluid delivery lumena can run from the proximal end to the distal end of the applicator tip, or from the proximal end to the interior of the applicator tip, such that a bolus of fluid may be released.

In a particular embodiment, the applicator tip distal end is a fluid permeable material, such as a cotton and gauze combination material or a sponge. These materials are known in the art for pledgets and are applicable here as well. The materials can include, but are not limited to, AUTOCOUNT® sponges, gelatin sponges, cellulose sponges, dextran sponges, cotton swabs, gauze wound dressings, fused gelatin beads or microspheres and others, as well as combinations thereof. In one embodiment, the tip distal end is cotton and gauze and the pledget attachment portion is a semi-solid material comprising a female threaded shaft.

In a further specific embodiment, there are methods of delivering a fluid to a target site within a body cavity comprising the steps of: coupling an applicator tip to a pledget attachment portion as described above, wherein the tip distal end and the pledget attachment portion become fluidly connected; coupling this tip proximal end to an applicator device wherein the tip proximal end and the applicator distal end become fluidly connected; and extruding at least one fluid, each from a source, through the applicator to the tip proximal end, through the tip to its distal end, from the tip distal end into the pledget, and from the pledget to the target site.

In an aspect of this method, two fluids are extruded and admixed within the pledget. The two fluids may be a thrombin solution and a fibrinogen solution. The thrombin may be animal-derived, or be recombinant human thrombin. The admixed solution can then be delivered to the target site by pressing the pledget on the target site. The pledget may be cotton, gauze, fused gelatin beads, or a sponge. In another aspect of this method, one fluid is extruded. The one fluid may be a low viscosity fluid, such as a thrombin solution. The low viscosity solution is delivered to the target site by pressing the pledget on the target site.

The embodiments and methods described herein can be useful when adapted for known applicator and minimally invasive (e.g., laparoscopic) applicator devices, and the present invention is not limited to a particular type of applicator. Typically, such applicators either house, or attach to, a reservoir containing the medicinal fluid. The fluid is expelled from the distal end of the applicator by a means at the proximal end of the applicator, typically employing gas, air, or manual pressure, and may include a ratcheted trigger system to overcome backflow. These applicators may be configured as syringes or elongated syringes (cannulated), in which the fluid is held within the applicator itself and dispensed by pressure on the proximal end of the applicator device. See WO 01/39669; FloSeal Laparoscopic Applicator (Baxter, UK). Alternatively, the applicator may have a "gun" configuration. See WO 02/064192. The applicator, instead of or inaddition to housing a reservoir, may also be in fluid communication with at least one external reservoir that contains the fluid(s) to be administered through the porous matrix of the tip and/or pledget. See, e.g., U.S. Pat. No. 6,228,051; FIBRIJET® 360° endoscopic applicator (Micromedics, Inc., St. Paul, Minn.). See also FIBRIJET® applicators (Micromedics, Inc., St. Paul, Minn.); and U.S. Patent application Pubs. No. 20030069537, No. 20020165483, No. 20070005007, and No. 20050096588. These various aspects provide the ability to continuously infuse the applicator tip with fresh solution (e.g., thrombin) while directly applying pressure to the site (e.g., the site of bleeding) in a broad range of circumstances. Additional applicator tips may be used with these devices for fluids with different viscoscities (e.g., gels) or to address additional surgical needs such as debridement or leave-behind applicator tips or pledgets.

In an alternative embodiment, the applicator tip and pledget are combined into a single tip device. In this embodiment, there is a method of delivering a fluid to a target site within a body cavity comprising the steps of: coupling a tip proximal end to an applicator (e.g., a minimally invasive applicator such as a laparoscopic device), wherein the tip proximal end and the applictor are fluidly connected; and extruding at least one fluid, each from a source, through the applicator to the tip proximal end to the tip distal end, and then to the target site. In an aspect of this method, two fluids are extruded and admixed within the tip distal end. For example, the two fluids may be a thrombin solution and a fibrinogen solution. The admixed solution can then be delivered to a target site by pressing the tip distal end on the target site. The applicator tip distal end may be cotton and gauze, or a sponge, etc. In another aspect of this method, one fluid is extruded. The one fluid may be a low viscosity fluid, such as a thrombin solution. The low viscosity solution is delivered to the target site by pressing the tip distal end on the target site.

In a further method of use, the tip and pledget or the applicator are useful for debridement of tissue, tissue translocation, absorption of fluid substances, and combinations thereof in a body cavity. In one aspect, the pledget or applicator tip is cotton and gauze, thus allowing the pledget or applicator tip to be pressed to a tissue and scrape tissue debris, move tissues and/or absorb fluids. Such can be accomplished through the properties of the material used to configure the pledget or applicator tip.

Another embodiment of the present invention provides for surgical kits comprising an applicator, tips, and thrombin. For example, the kit contains an applicator with at least one detachable tip or pledget that allows for continuous application of thrombin through the tip, so that the surgeon or member of the surgical team can apply thrombin and concurrent pressure in surgery procedures. More specifically, the kit may include a minimally invasive (e.g., laparoscopic) applicator co-packaged with one or more detachaeable tips and thrombin, for example, recombinant human thrombin, such as 5,000 IU recombinant human thrombin. This gives the surgeon the ability to continuously infuse a cotton applicator tip with thrombin solution while directly applying pressure to the site of bleeding. The thrombin may be in solution, e.g., in saline solution, or may be a viscous solution such as a "flowable" microsphere/thrombin gel-like formulation. Additionally, the applicator tips may be configured to allow for debridement, or the tips or pldgets may be be constructed of biodegradable, bioabsorbable materials that may be left at the site of bleeding.

From the foregoing, it will be appreciated that, although specific embodiments of the invention have been described herein for purposes of illustration, various modifications may be made without deviating from the spirit and scope of the invention.

What is claimed is:

1. A device for delivery of a first solution comprising a recombinant protein comprising human thrombin and a second solution to a bleeding surgical site of a human patient, the device comprising:
an applicator comprising at least two fluid delivery lumena in fluid communication with a source of the first solution and a source of the second solution, the applicator having a proximal end and a distal end;
an applicator tip having a proximal end and a distal end and comprising at least two delivery lumena, wherein the applicator tip proximal end is configured to detachably connect to the distal end of the applicator by a semi-pliable flange-mount such that the at least two delivery lumena of the applicator tip are each in fluid communication with the fluid delivery lumen of the applicator; and
a fluid-permeable porous matrix pledget configured to deliver the recombinant protein comprising human thrombin when pressed against the surgical site, wherein the pledget is configured to detachably couple to the applicator tip distal end such that the pledget is in fluid communication with the at least two delivery lumena of the applicator tip;
wherein the device is configured for minimally invasive, laparoscopic delivery of the recombinant protein comprising human thrombin to the surgical site;
wherein the applicator has a rigidity such that a user can manipulate the proximal end of the applicator to apply an effective amount of pressure with the pledget to the surgical site such that bleeding is reduced concurrently while continuously delivering the first solution and the second solution when the pledget is pressed against the surgical site;
wherein the first solution and the second solution delivered from the two delivery lumena mix upon entering the pledget;
wherein the applicator further comprises an interior shaft; and
wherein the distal end of the applicator comprises at least two spring arms comprising retaining teeth to secure the flange mount.

2. The device of claim 1, wherein at least one fluid delivery lumen of the applicator tip is a branched fluid delivery lumen.

3. The device of claim 1, wherein the pledget comprises gelatin, a cotton gauze, a sponge, a plastic, fused gelatin beads, or a combination thereof.

4. The device of claim 1, wherein the pledget comprises biocompatible, bioabsorbable material that, in use, can be left permanently at the surgical site.

5. The device of claim 1, wherein the applicator tip has a diameter of about 5-15 mm.

6. The device of claim 1, wherein the applicator tip has a length of about 10-20 mm.

7. The device of claim 1, wherein the recombinant protein comprising human thrombin comprises 5,000 IU recombinant human thrombin.

8. The device of claim 1, wherein the first solution and the second solution mix externally to the applicator.

9. The device of claim 1, wherein the second solution comprises fibrinogen.

10. The device of claim 1, wherein the flange mount comprises at least two fluid delivery lumena.

11. The device of claim 1, wherein the interior shaft comprises a tapered tip, such that the tapered tip fits into the flange mount on the proximal end of the applicator tip.

12. The device of claim 1, further comprising a handle configured to connect to the at least two spring arms, such that squeezing the handle retracts the spring arms and allows the flange mount to be released when the interior shaft advances along the distal end of the applicator.

13. A device for delivery of a first fluid and a second fluid to a bleeding surgical site of a human patient, the device comprising:
an applicator comprising at least two fluid delivery lumena, the applicator having a proximal end and a distal end;
an applicator tip having a proximal end and a distal end and comprising at least two fluid delivery lumena, wherein the applicator tip proximal end is configured to detachably connect to the distal end of the applicator by a semi-pliable flange-mount such that the at least two fluid delivery lumena of the applicator tip are each in fluid communication with the fluid delivery lumen of the applicator; and
a fluid-permeable porous matrix pledget configured to deliver fluid when pressed against the surgical site, wherein the pledget is configured to detachably couple to the applicator tip distal end such that the pledget is in fluid communication with the at least two fluid delivery lumena of the applicator tip;
wherein the device is configured for minimally invasive, laparoscopic delivery of the fluid;
wherein the applicator has a rigidity such that a user can manipulate the proximal end of the applicator to apply an effective amount of pressure with the pledget to the surgical site such that bleeding is reduced concurrently while continuously delivering the first fluid and second fluid when the pledget is pressed against the surgical site;
wherein the first fluid and the second delivered from the two delivery lumena mix upon entering the pledget;
wherein the applicator further comprises an interior shaft; and wherein the distal end of the applicator comprises at least two spring arms comprising retaining teeth to secure the flange mount.

14. The device of claim 13, wherein at least one fluid delivery lumen of the applicator tip is a branched fluid delivery lumen.

15. The device of claim 13, wherein the pledget comprises gelatin, a cotton gauze, a sponge, a plastic, fused gelatin beads, or a combination thereof.

16. The device of claim 13, wherein the pledget comprises biocompatible, bioabsorbable material that, in use, can be left permanently at the surgical site.

17. The device of claim 13, wherein the pledget is configured for the mixing of two fluids.

18. The device of claim 13, wherein the applicator tip has a diameter of about 5-15 mm.

19. The device of claim 13, wherein the at least two fluid delivery lumena of the applicator are in fluid communication with a source of the first fluid and a source of the second fluid.

20. The device of claim 19, wherein the first fluid comprises a recombinant protein comprising human thrombin.

21. The device of claim 20, wherein the second fluid comprises fibrinogen.

22. The device of claim 13, wherein the device is configured for the delivery of a gel.

23. The device of claim 13, wherein the first fluid and the second fluid mix externally to the applicator.

24. The device of claim 13, wherein the flange mount comprises at least two fluid delivery lumena.

25. The device of claim 13, wherein the interior shaft comprises a tapered tip, such that the tapered tip fits into the flange mount on the proximal end of the applicator tip.

26. The device of claim 13, further comprising a handle configured to connect to the at least two spring arms, such that squeezing the handle retracts the spring arms and allows the flange mount to be released when the interior shaft advances along the distal end of the applicator.

27. A device for delivery of a first solution comprising a recombinant protein comprising human thrombin and a second solution to a bleeding surgical site of a human patient, the device comprising:
an applicator comprising at least two fluid delivery lumena in fluid communication with a source of the first solution and a source of the second solution,
an applicator tip comprising at least two delivery lumena coupled to the applicator by a semi-pliable flange-mount such that the at least two delivery lumena of the applicator tip are each in fluid communication with the fluid delivery lumen of the applicator; and
a fluid-permeable porous matrix pledget coupled to the applicator tip such that the pledget is in fluid communication with the at least two delivery lumena of the applicator tip, the pledget being configured to deliver the recombinant protein comprising human thrombin when pressed against the surgical site;
wherein the device is configured for minimally invasive, laparoscopic delivery of the recombinant protein comprising human thrombin to the surgical site;
wherein the applicator has a rigidity such that a user can manipulate the proximal end of the applicator to apply an effective amount of pressure with the pledget to the surgical site such that bleeding is reduced concurrently while continuously delivering the first solution and the second solution when the pledget is pressed against the surgical site;
wherein the first solution and the second solution delivered from the two delivery lumena mix upon entering the pledget;
wherein the applicator further comprises an interior shaft; and
wherein the distal end of the applicator comprises at least two spring arms comprising retaining teeth to secure the flange mount.

28. The device of claim 27, wherein at least one fluid delivery lumen of the applicator tip is a branched fluid delivery lumen.

29. The device of claim 27, wherein the pledget comprises gelatin, a cotton gauze, a sponge, a plastic, fused gelatin beads, or a combination thereof.

30. The device of claim 27, wherein the pledget comprises biocompatible, bioabsorbable material that, in use, can be left permanently at the surgical site.

31. The device of claim 27, wherein the applicator tip has a diameter of about 5-15 mm.

32. The device of claim 27, wherein the applicator tip has a length of about 5 mm-25 mm.

33. The device of claim 27, wherein the recombinant protein comprising human thrombin comprises 5,000 IU recombinant human thrombin.

34. The device of claim 27, wherein the first solution and the second solution mix externally to the applicator.

35. The device of claim 27, wherein the second solution comprises fibrinogen.

36. The device of claim 27, wherein the flange mount comprises at least two fluid delivery lumena.

37. The device of claim 27, wherein the interior shaft comprises a tapered tip, such that the tapered tip fits into the flange mount on the proximal end of the applicator tip.

38. The device of claim 27, further comprising a handle configured to connect to the at least two spring arms, such that squeezing the handle retracts the spring arms and allows the flange mount to be released when the interior shaft advances along the distal end of the applicator.

* * * * *